United States Patent
Boxall

(10) Patent No.: US 8,505,542 B2
(45) Date of Patent: Aug. 13, 2013

(54) INFANT HAND RESTRAINT WITH DIAPER

(76) Inventor: MeriAnn Boxall, Magna, UT (US)

( * ) Notice: Subject to any disclaimer, the term of this patent is extended or adjusted under 35 U.S.C. 154(b) by 199 days.

(21) Appl. No.: 12/966,141

(22) Filed: Dec. 13, 2010

(65) Prior Publication Data

US 2011/0168190 A1    Jul. 14, 2011

Related U.S. Application Data

(60) Provisional application No. 61/295,127, filed on Jan. 14, 2010.

(51) Int. Cl.
*A61F 5/37* (2006.01)

(52) U.S. Cl.
USPC .................................................. 128/879

(58) Field of Classification Search
USPC ............... 128/869, 872, 878, 879, 880, 881, 128/882; 602/20, 21, 22; 604/392
See application file for complete search history.

(56) References Cited

U.S. PATENT DOCUMENTS

| | | | |
|---|---|---|---|
| 1,288,170 A | 12/1918 | Pick | |
| 1,310,958 A | 7/1919 | O'Connor | |
| 2,180,270 A | 11/1939 | Anderson, Jr. | |
| 2,295,806 A | 9/1942 | Peterson | |
| 2,425,489 A | 8/1947 | Peterson | |
| 3,324,851 A | 6/1967 | Posner | |
| 4,172,453 A | 10/1979 | Leckie | |
| 4,610,244 A | 9/1986 | Hammond | |
| 4,860,560 A * | 8/1989 | Lundelius | 70/16 |
| 5,016,650 A * | 5/1991 | Marlar | 128/878 |
| 5,358,500 A * | 10/1994 | Lavon et al. | 604/385.29 |
| 6,371,951 B1 * | 4/2002 | Koczab et al. | 604/385.24 |
| 6,406,469 B1 * | 6/2002 | Brain et al. | 604/394 |
| 6,935,342 B2 * | 8/2005 | Larson | 128/869 |
| 8,235,926 B2 * | 8/2012 | Houchin | 602/20 |
| 2004/0149293 A1 | 8/2004 | Freedman | |
| 2009/0036813 A1 | 2/2009 | Whitney | |

* cited by examiner

*Primary Examiner* — Patricia Bianco
*Assistant Examiner* — Raymond E Harris

(57) ABSTRACT

A hand restraint/cloth diaper combination can be used any time an infant needs to have their hands restrained from touching their heads or other parts of their body. The restraint device of the present invention allows for an infant to have muscle exercise and movement, while still allowing the diaper to be changed. The restraint device may be adjusted to keep the arms to be restrained right next to the infant's hips for travel or sitting and may be further adjusted to allow increased movement for laying and exercise. The restraint device may include a cloth diaper, an elastic waistband on the cloth diaper, an extra elastic band adapted to run around the back of the infant, and adjustable arm cuffs.

1 Claim, 2 Drawing Sheets

INFANT HAND RESTRAINT WITH DIAPER

CROSS-REFERENCE TO RELATED APPLICATIONS

This application claims the benefit of priority of U.S. Provisional patent application number 61/295,127, filed Jan. 14, 2010, which is herein incorporated by reference.

BACKGROUND OF THE INVENTION

The present invention relates to infant hand restraints and, more particularly, to an infant hand restraint with a cloth diaper, elastic waistband, extra elastic band in back, and adjustable arm cuffs.

When an infant has surgery on their head or face, for example a cleft lip surgery, they are required following the surgery to have their arms restrained away from their face to protect the incision for a minimum of one month. This is difficult for the child, but very important to the success of the surgery. With current medical devices, which keep the arms straight to the side in a device holding only the arms, movement and muscle exercise is not permitted and rubbing under the arms may create sores.

As can be seen, there is a need for an infant hand restraint device that may allow movement of the arms to exercise growing muscles while keeping hands away from the infant's face.

SUMMARY OF THE INVENTION

In one aspect of the present invention, a restraint device comprises a diaper having an elastic waistband and leg holes; an additional elastic attached to one side of the elastic waistband; at least one strap attached to the diaper; and at least one arm cuff attached to the at least one strap.

In another aspect of the present invention, a restraint device comprises a cloth diaper having an elastic waistband and leg holes; an additional elastic attached to one side of the elastic waistband; at least one strap attached to the diaper; at least one arm cuff attached to the at least one strap; a first fastener connected to the strap proximal to the diaper; at least one mating fastener connected to the strap, distal the first fastener relative to the diaper, wherein the mating fastener is adapted to fasten to the first fastener; and an arm cuff fastener attached to the arm cuff, the arm cuff fastener adapted to fasten to the first fastener.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, an embodiment of the present invention provides a hand restraint/cloth diaper combination that can be used any time an infant needs to have their hands restrained from touching their heads or other parts of their body. The restraint device of the present invention allows for an infant to have muscle exercise and movement, while still allowing the diaper to be changed. The restraint device may be adjusted to keep the arms to be restrained right next to the infant's hips for travel or sitting and may be further adjusted to allow increased movement for laying and exercise. The restraint device may include a cloth diaper, an elastic waistband on the cloth diaper, an extra elastic band adapted to run around the back of the infant, and adjustable arm cuffs.

The restraint device of the present invention may be used for infant/children that have had mouth surgery, head or face surgery or reconstruction dental issues, for children with disabilities that need to have their hands restrained for any reason. The restraint device could be used to keep a child from sucking their thumb, or biting their hands, and also used in the hospital after any surgery to keep a child from interfering with their IV's, tubes, or other medical devices. The restraint device may be used to restrain either one or both arms of the infant.

Figure 1:
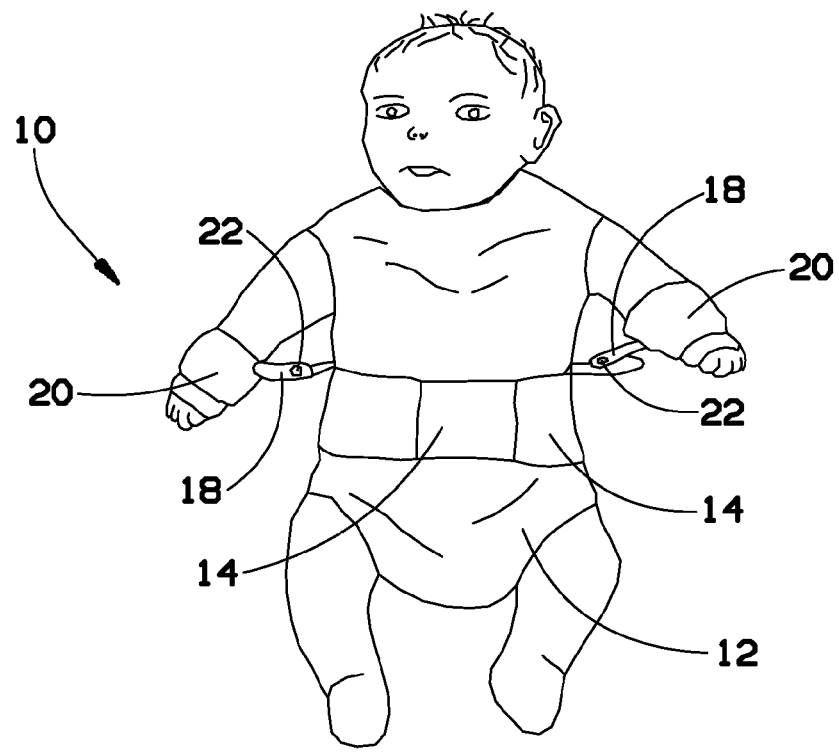
FIG. 1 is a perspective view of an infant using the restraint device according to an exemplary embodiment of the present invention.
Figure 2:
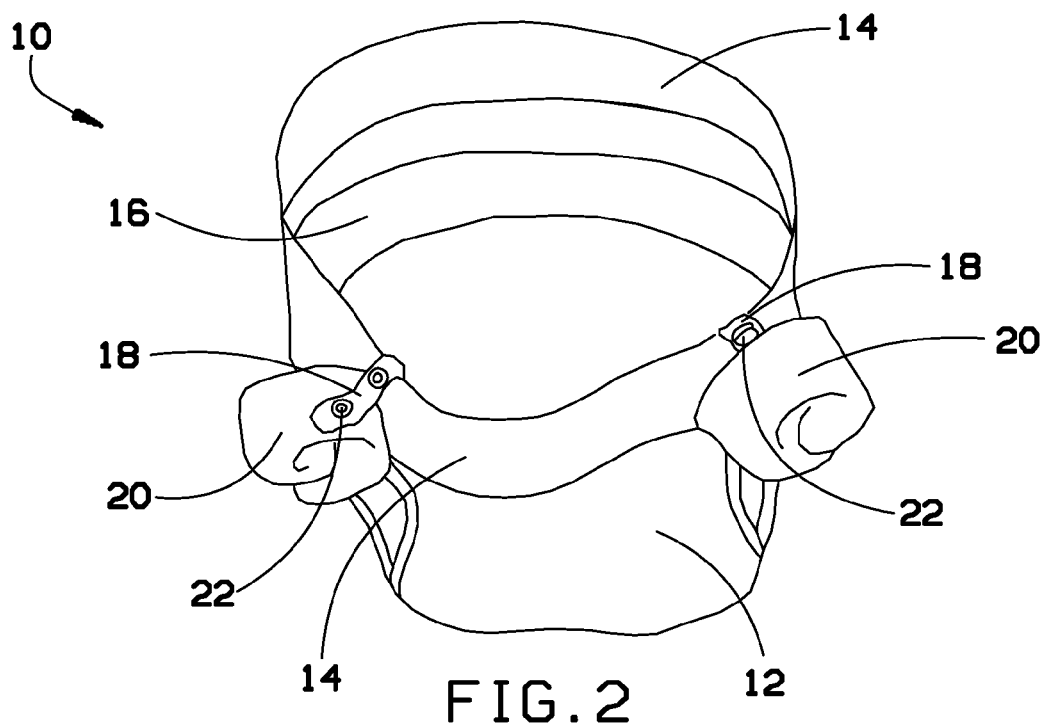
FIG. 2 is a perspective view of the restraint device of FIG. 1.
Figure 3:
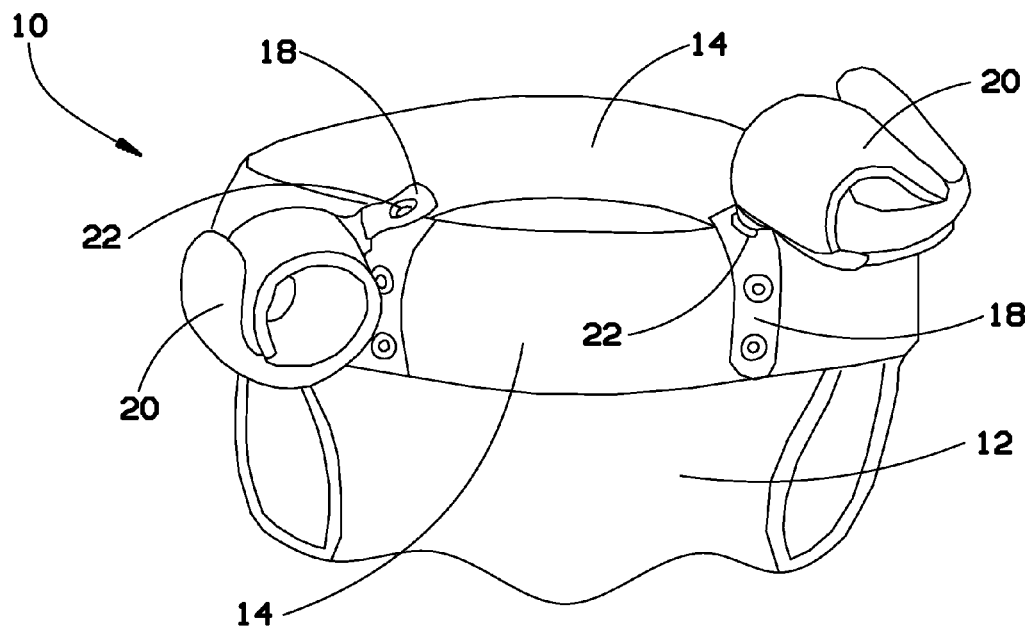
FIG. 3 is a front view of the restraint device of FIG. 1.
Figure 4:
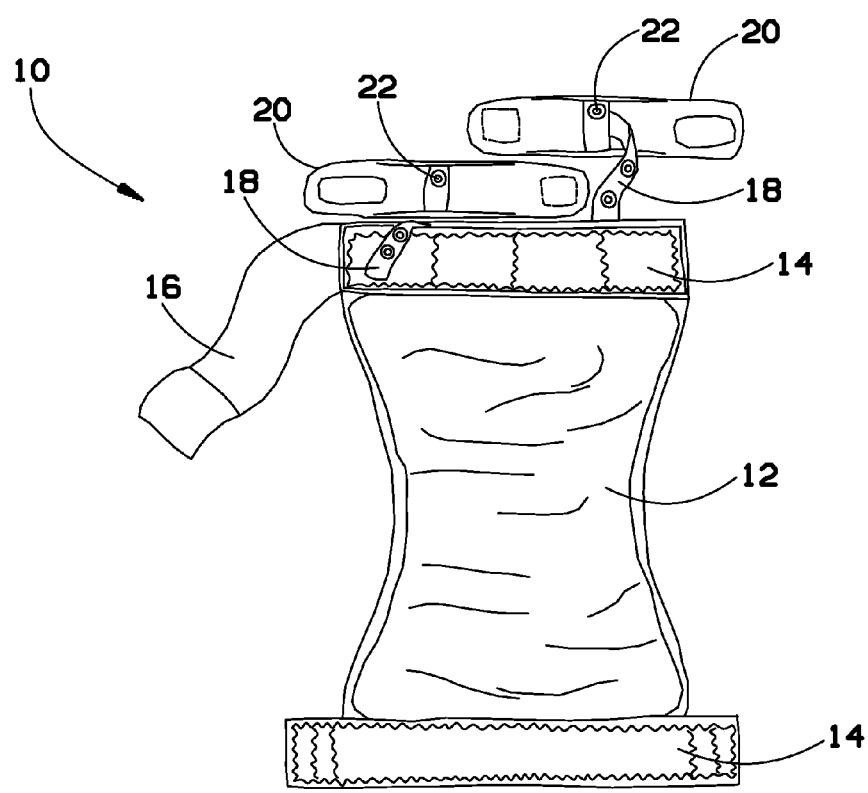
FIG. 4 is a folded-out view of the restraint device of FIG. 1.

Referring to FIGS. 1 through 4, a restraint device 10 may include a cloth diaper 12 that may go around an infant's waist and through the infant's legs. The diaper 12 may be made with any type of soft flexible fabric, typically with elastic around the infant's legs. The diaper 12 may include an elastic waistband 14. As shown in FIG. 4, the elastic waistband 14 may include a front waistband 14 and a rear waistband 14. The front and rear waistbands 14 may have fasteners to connect them together. In some embodiments, the waistbands 14 may include hook and loop type fasteners, such as Velcro® to allow the waistband 14 to be adjusted to fit most infant sizes. The elastic waistband 14 may be any suitable size, typically about 2 inches in width for sufficient support.

An additional elastic 16 may be sewn on to the front of the diaper 12, on one side of the waistband 14. The additional elastic 16 may loop around the back of the infant to attach on the other side with a hook and loop fastener, for example. This additional elastic 16 may have a width of about 1.5 inches. This additional elastic 16 may attach inside the front flap's elastic waistband 14, while the other elastic may attach to the outside of the front flap.

Two straps 18 may be attached, for example, by sewing, into the diaper 12, typically on the waistband 14. The straps 18 may attach to the inside of the front flap and have four or more fasteners 22, such as snaps, formed therealong. The straps 18 may be made of any suitable material, such as nylon or other lightweight material. The fasteners 22 may be used with one receiving fastener side at the diaper end of the strap 18 (such as a female snap), and two or more opposite connectors (such as male snaps) at the middle and top of the strap 18. This placement of fasteners 22 allows the strap 18 to achieve different lengths.

Arm cuffs 20 can be made of any type of soft fabric, such as fleece, flannel, cotton or the like. The arm cuffs 20 may attach around the arms of the infant and connect with a fastener, such as a hook and loop fastener, hooks, clips, or snaps. The arm cuffs 20 may have a fastener 22 (such as another male snap) to allow it to connect to the very bottom of the strap 18, near the diaper. The fasteners 22 may allow the arm cuffs 20 to be positioned close to the infant's side, or at various distances away from the infant's side, depending on which fasteners 22, if any, are connected.

The cloth diaper 12 may wrap around the waist and through the legs of the infant. This configuration prevents the child from being able to pull up and get their hands to their face. The elastic waistband may allow the device 10 to fit comfortably around most infant's waists and helps to keep the cloth diaper down and in place. The additional elastic 16 may connect around the back of the child to the front to allow for the actual diaper (not shown) to be changed on the child. This feature may allow a period of time for the cloth diaper 12 to be partially removed while still keeping the face protected from the hands.

The restraint device 10 may be made by conventional processes known to those skilled in the art. For example, components may be cut out and sewn together according to conventional methods.

It should be understood, of course, that the foregoing relates to exemplary embodiments of the invention and that modifications may be made without departing from the spirit and scope of the invention as set forth in the following claims.

What is claimed is:

1. A restraint device comprising:
   a cloth diaper having an elastic waistband and leg holes;
   an additional elastic attached to one side of the elastic waistband;
   at least one strap attached to the diaper;
   at least one arm cuff attached to the at least one strap;
   a first fastener connected to the at least one strap proximal to the diaper;
   at least one mating fastener connected to the at least one strap, distal the first fastener relative to the diaper, wherein the mating fastener is adapted to fasten to the first fastener;
   an arm cuff fastener attached to the at least one arm cuff, the arm cuff fastener adapted to fasten to the first fastener;
   wherein the elastic waistband includes a front waistband and a rear waistband on a front side and a back side of the cloth diaper, the front and rear waistbands adapted to fasten together;
   wherein the at least one arm cuff is configured to prevent a child from pulling UP a hand of the child to a face of the child; and
   wherein the additional elastic is configured to connect around the back of the child to the front of the child to allow for the cloth diaper to be partially removed while keeping the face of the child protected from the hand of the child.

* * * * *